(12) United States Patent
Mertz

(10) Patent No.: US 8,198,604 B2
(45) Date of Patent: Jun. 12, 2012

(54) SYSTEM AND METHOD FOR PROVIDING ENHANCED BACKGROUND REJECTION IN THICK TISSUE WITH DIFFERENTIAL-ABERRATION TWO-PHOTON MICROSCOPY

(75) Inventor: Jerome Mertz, Boston, MA (US)

(73) Assignee: Trustees of Boston University, Boston, MA (US)

( * ) Notice: Subject to any disclaimer, the term of this patent is extended or adjusted under 35 U.S.C. 154(b) by 441 days.

(21) Appl. No.: 12/240,074

(22) Filed: Sep. 29, 2008

(65) Prior Publication Data

US 2009/0084980 A1  Apr. 2, 2009

Related U.S. Application Data

(60) Provisional application No. 60/975,855, filed on Sep. 28, 2007.

(51) Int. Cl.
*G01N 21/64* (2006.01)
(52) U.S. Cl. ............ 250/458.1; 351/205; 356/512
(58) Field of Classification Search ........ 250/458.1; 351/205; 356/512
See application file for complete search history.

(56) References Cited

U.S. PATENT DOCUMENTS

| | | | | |
|---|---|---|---|---|
| 5,305,074 A * | 4/1994 | Feldman | ............ | 356/512 |
| 7,564,622 B2 * | 7/2009 | Ishiwata | ............ | 359/385 |
| 7,576,316 B2 * | 8/2009 | Seyfried et al. | ............ | 250/252.1 |
| 2001/0003488 A1 * | 6/2001 | Yoshida | ............ | 359/381 |
| 2003/0071969 A1 * | 4/2003 | Levine et al. | ............ | 351/221 |
| 2003/0147046 A1 * | 8/2003 | Shadduck | ............ | 351/159 |
| 2004/0057054 A1 * | 3/2004 | Toyooka et al. | ............ | 356/496 |
| 2004/0059526 A1 * | 3/2004 | Toyooka et al. | ............ | 702/57 |
| 2004/0100704 A1 * | 5/2004 | Shadduck | ............ | 359/819 |
| 2005/0168808 A1 * | 8/2005 | Ishiwata | ............ | 359/368 |
| 2006/0033933 A1 * | 2/2006 | Feierabend et al. | ............ | 356/512 |
| 2006/0238710 A1 * | 10/2006 | Dick et al. | ............ | 351/211 |
| 2007/0046948 A1 * | 3/2007 | Podoleanu et al. | ............ | 356/497 |
| 2007/0200052 A1 * | 8/2007 | Seyfried et al. | ............ | 250/201.3 |
| 2007/0253057 A1 * | 11/2007 | Potsaid et al. | ............ | 359/384 |
| 2008/0278683 A1 * | 11/2008 | Su et al. | ............ | 351/205 |
| 2009/0073563 A1 * | 3/2009 | Betzig | ............ | 359/578 |
| 2009/0137990 A1 * | 5/2009 | Sheinis | ............ | 606/5 |

\* cited by examiner

*Primary Examiner* — David Porta
*Assistant Examiner* — Djura Malevic
(74) *Attorney, Agent, or Firm* — Peter A. Nieves; Sheehan Phinney Bass + Green PA

(57) ABSTRACT

A system for providing enhanced background rejection in thick tissue contains an aberrating element for introducing controllable extraneous spatial aberrations in an excitation beam path; at least one mirror capable of directing received laser pulses to the aberrating element; an objective; a beam scanner imaged onto a back aperture of the objective so that the beam scanner steers beam focus within the thick tissue; and a detector for recording signals produced by the tissue. An associated method comprises the steps of acquiring two-photon excited fluorescence of thick tissue without extraneous aberrations; introducing an extraneous aberration pattern in an excitation beam path; acquiring two-photon excited fluorescence of the thick tissue having the introduced extraneous aberration pattern; and subtracting the two-photon excited fluorescence with extraneous aberrations from the acquired standard two-photon excited fluorescence of the thick tissue without extraneous aberrations.

16 Claims, 5 Drawing Sheets

SYSTEM AND METHOD FOR PROVIDING ENHANCED BACKGROUND REJECTION IN THICK TISSUE WITH DIFFERENTIAL-ABERRATION TWO-PHOTON MICROSCOPY

CROSS-REFERENCE TO RELATED APPLICATION

This application claims priority to copending U.S. Provisional Application entitled, "Enhanced Background Rejection In Thick Tissue With Differential-Aberration Two-Photon Microscopy," having Ser. No. 60/975,855, filed Sep. 28, 2007, which is entirely incorporated herein by reference.

GOVERNMENT SUPPORT

This invention was made with Government Support under Contract No. EB005736 awarded by the National Institutes of Health. The Government has certain rights in the invention.

FIELD OF THE INVENTION

The present invention is generally related to imagine, and more particularly is related to deep tissue imaging.

BACKGROUND OF THE INVENTION

The statements in this section merely provide background information related to the present disclosure and may not constitute prior art.

When a two-photon excited fluorescence (TPEF) microscope is used to image deep tissue, out-of-focus background can arise from both ballistic and non-ballistic excitation. TPEF microscopy has become a well-established tool for high-resolution imaging in scattering media such as thick tissue. While it is well accepted that TPEF microscopy provides greater imaging depth penetration in thick tissue than more conventional fluorescence imaging techniques, such as confocal or widefield microscopy, the depth penetration of TPEF microscopy remains nonetheless limited. For example, demonstrations of TPEF imaging beyond 500 pm in brain tissue have been rare.

Several factors limit TPEF microscopy depth penetration in thick tissue, three of which are described below for exemplary purposes:

1) An excitation beam can undergo scattering when it propagates through tissue. This scattering weakens the ballistic (un-scattered) excitation power that attains the beam focus and thereby reduces the TPEF signal generated at the focus. Since scattering scales roughly exponentially with propagation distance, by dint of the Lambert-Beer law, the reduction in TPEF signal becomes particularly severe at larger focal depths. One strategy to maintain adequate ballistic excitation power at relatively large focal depths has involved the use of non-standard laser sources based on regenerative amplifiers. Unfortunately, such a strategy can only go so far in compensating for an exponential loss in ballistic power, even though it has been the most successful to date in pushing the limits of depth penetration.

2) The required increase in excitation power necessary to maintain (or try to maintain) adequate ballistic power at the beam focus can lead to significant power densities near the tissue surface. If the tissue is fluorescent near its surface, as is the case for example if the fluorescent labeling is homogeneously distributed throughout the sample, or if the sample is autofluorescent either intrinsically or due to superficial tissue damage, then the power density of the ballistic light near the surface can be so high as to produce out-of-focus background fluorescence that is non-negligible compared to the in-focus signal fluorescence. When this background fluorescence begins to dominate signal fluorescence, there is no point in attempting to image deeper in the tissue.

3) At depths where the scattered light is so strong and the ballistic light so weak that the power density of the ballistic light cannot compete with that of the scattered light near the beam focus, then again there is no point in attempting to image deeper in the tissue. Inasmuch as scattering in biological tissue is very dominantly forward directed, the scattered light that exhibits the greatest power density is the light that is only slightly deviated from its ballistic path, as can be verified by Monte-Carlo simulation. Light paths that are only slightly deviated are often referred to as "snakelike", as opposed to the more severely scattered "diffusive" paths. Snakelike scattering leads to a blurred halo of background fluorescence surrounding the in-focus signal fluorescence. While at shallow depths, this background halo is usually negligible compared to the signal, at larger depths the background halo can become quite problematic.

Thus, a heretofore unaddressed need exists in the industry to increase depth penetration of TPEF microscopy and to address the aforementioned deficiencies and inadequacies.

SUMMARY OF THE INVENTION

Embodiments of the present invention provide a system and method for rejecting out-of-focus background in a laser scanning nonlinear microscope (such as a TPEF microscope). Briefly described, in architecture, one embodiment of the system, among others, can be implemented as follows. An apparatus for providing enhanced background rejection in thick tissue, comprises: an aberrating element located in an excitation beam path of the apparatus, wherein the aberrating element is capable of introducing extraneous spatial aberrations in the excitation beam path of the apparatus; at least one mirror capable of directing received laser pulses to the aberrating element; an objective; a beam scanner imaged onto a back aperture of the objective so that the beam scanner steers beam focus within the thick tissue; and a detector for recording signals produced by the tissue,
wherein there is no communication between the deformable mirror and the detector.

The present invention can also be viewed as providing methods for modulating the in-focus signal in a laser scanning nonlinear microscope, thereby enabling a better discrimination of in-focus signal from out-of-focus background. In this regard, one embodiment of such a method, among others, can be broadly summarized by the following steps: acquiring a standard two-photon excited fluorescence of thick tissue without extraneous aberrations; introducing an extraneous aberration pattern in an excitation beam path; acquiring two-photon excited fluorescence of the thick tissue having the introduced extraneous aberration pattern, providing a two-photon excited fluorescence with extraneous aberrations; and subtracting the two-photon excited fluorescence with extraneous aberrations from the acquired standard two-photon excited fluorescence of the thick tissue without extraneous aberrations resulting in an enhanced out-of-focus two-photon excited fluorescence background rejection.

By acquiring two images with different aberration states of the laser illumination (typically with and without extraneous aberrations), a final image can be obtained by numerical processing that exhibits enhanced rejection of out-of-focus background.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION

The present system and method provides a robust technique that significantly alleviates limitations to depth penetration of TPEF microscopy arising from out-of-focus background generated either by superficial ballistic excitation or by snakelike scattered excitation. The present system and method uses an aberrating element, such as, but not limited to, a deformable mirror, in an excitation light path. While in most applications involving a deformable mirror, the deformable mirror is meant to improve beam focus by compensating for sample-induced aberrations, in the present system and method the deformable mirror is meant to do just the opposite. Instead, the deformable mirror is used in the present system and method to introduce extraneous spatial aberrations in an excitation beam path so as to purposefully degrade the quality of the ballistic light focus, thereby quenching the TPEF signal and associated focal spot.

While the TPEF signal can be severely quenched with extraneous aberrations, the TPEF background generated by superficial ballistic excitation remains relatively unaffected. Subtraction of a TPEF image acquired with aberrations (background image) from a TPEF image acquired without aberrations (standard image) then recovers the TPEF signal and associated focal spot, while rejecting most of this superficial background. This technique is referred to herein as differential-aberration (DA) imaging. It should be noted that while the present description uses the example of the aberrating element being a deformable mirror, the aberrating element is not intended to be limited to a deformable mirror, but instead may be a different aberrating element.

Figure 1:
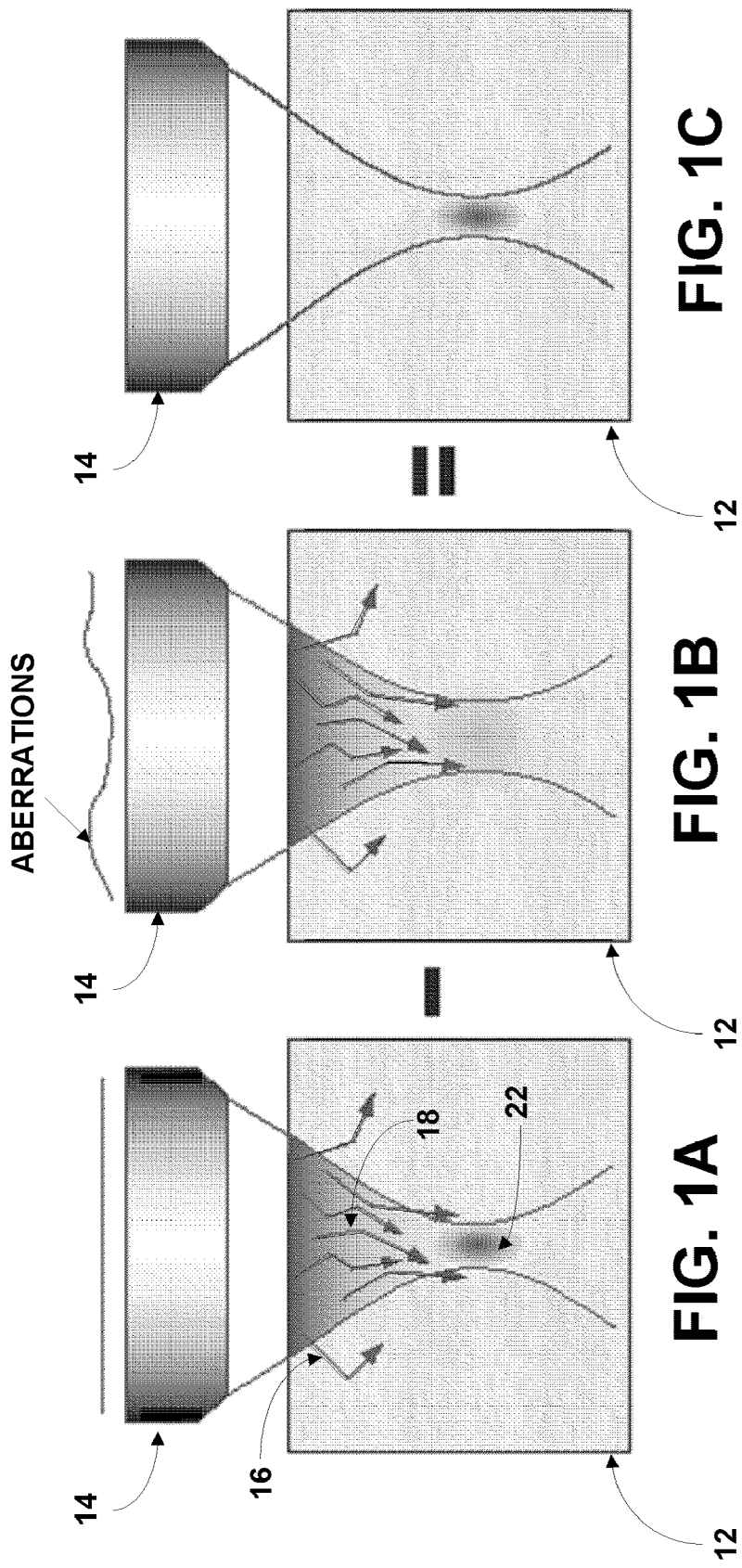
FIG. 1A, FIG. 1B, and FIG. 1C are schematic diagrams illustrating the general principle of differential-aberration two-photon excited fluorescence (DA-TPEF), in accordance with the present system and method.

FIG. 1A, FIG. 1B, and FIG. 1C are schematic diagrams illustrating the general principle of differential-aberration two-photon excited fluorescence (DA-TPEF), in accordance with the present system and method. Specifically, when focusing a laser beam 10 into thick tissue 12, such as by use of an objective 14, as described hereinafter with regard to FIG. 2, power of the laser beam 10 becomes largely depleted by scattering before the laser attains the beam focus. As shown by FIG. 1A, TPEF background can then arise from out-of-focus ballistic excitation 16, particularly near the sample (also referred to as a medium) 12 surface, or from "snakelike" scattered excitation 18 near the beam focus 22, both of which can produce background fluorescence that is non-negligible compared to in-focus TPEF signal 20 fluorescence.

As shown by FIG. 1B, in accordance with the present invention, the introduction of extraneous aberrations 24 in an illumination pupil, or objective 14, leads to a spreading of the ballistic excitation profile that is more pronounced near the beam focus 22 than away from the beam focus 22, thereby preferentially quenching the in-focus TPEF signal 20 and associated focal spot, while leaving the out-of-focus TPEF background relatively unchanged. As shown herein, in accordance with the present invention, the subtraction of a TPEF image with extraneous aberrations, as shown by FIG. 1B from an image without extraneous aberrations, as shown by FIG. 1A, results in an enhanced out-of-focus TPEF background rejection, as shown by FIG. 1C. This process is described in more detail below.

Figure 2:
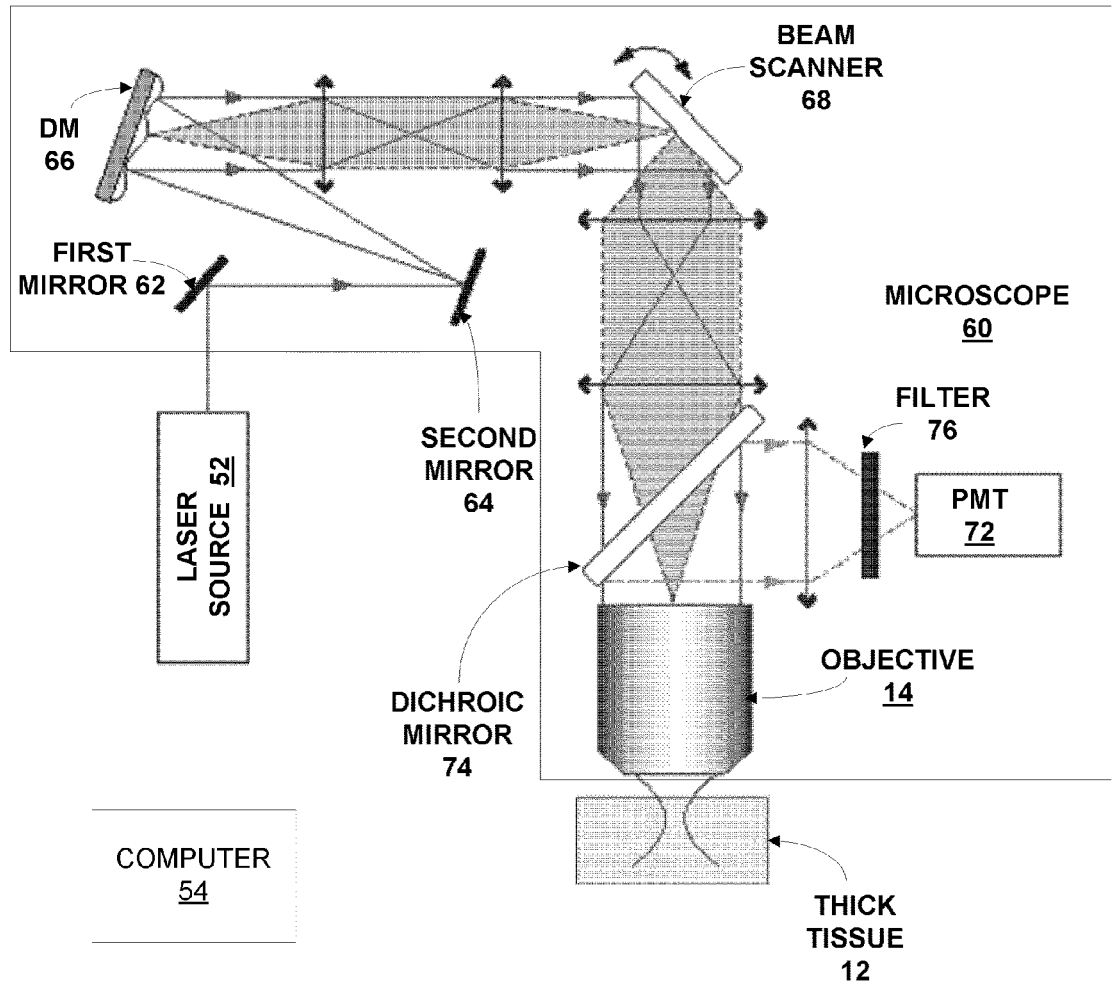
FIG. 2 provides an example of a system that may be used in accordance with the present invention.

An example of a system 50 that may be used in accordance with the present invention, is illustrated by FIG. 2. In accordance with one exemplary embodiment of the invention, the system 50 contains a laser source 52, a computer 54, a two-photon excited fluorescence microscope with the addition of a differential aberrating element (DA-TPEF) 60. The laser source 52 may be one of many categories of pulse laser sources used for providing non-linear interactions in matter. As an example, the laser source 52 may be a Titanium-sapphire (Ti:Sa) laser. Of course, the laser source 52 is not intended to be limited to a Ti:Sa laser.

A pulse laser of the laser source 52 is directed to the DA-TPEF microscope 60. As is shown by FIG. 2, the microscope 60 contains a first mirror 62 and a second mirror 64 for directing laser pulses from the laser source 52 to a deformable mirror 66. It should be noted that the microscope 60 may have more or fewer mirrors for directing laser pulses from the laser source 52 to the deformable mirror 66. It should also be noted that the deformable mirror 66 is only an example of a switchable aberrating element. Other types of switchable aberrating elements could also be implemented.

The deformable mirror 66 is located in an excitation beam path of the microscope 60. The deformable mirror 66 is, in turn, imaged onto a beam scanner 68. The beam scanner 68 is imaged onto a back aperture of the objective 14, so that, ultimately, the beam scanner 68 steers the beam focus within the sample of interest. The deformable mirror 66 is therefore located in a conjugate plane of the objective 14 back aperture, meaning that height deformations in the deformable mirror 66 effectively translate to phase deformations (aberrations) in the pupil function governing the excitation beam focus. The deformable mirror 66 may provide one or more of many aberration profiles, such as, but not limited to, quadrant or spiral phase aberration profiles. Such profiles would be caused by providing different voltage patterns to the deformable mirror 66.

An example of a deformable mirror that may be used in accordance with the present system and method includes, but is not limited to, a pDMS-Multi deformable mirror with a 3.5 maximum stroke, by Boston Micromachines Corporation, of Cambridge, Mass.

TPEF resulting from the laser source 52 is collected (typically through the microscope objective) and directed onto a detector, typically with the use a dichroic mirror 74. The detector records the signal produced by the sample and can be, but is not restricted to, a photomultiplier tube (PMT) 72. The dichroic mirror 74, if used, separates laser illumination from the signal produced by the sample. It should be noted that there is no communication between the deformable mirror 66 and the PMT 72, as a result, patterns are applied to the deformable mirror 66 that are independent of what is received by the PMT 72.

The microscope 60 also can contain a filter 74 that is capable of removing stray laser light prior to signal being received by the PMT 72.

The present system and method enables a separation of the excitation light from the laser source 52 into two components, namely, ballistic and scattered. These are respectively defined as the components of the excitation light that have not and have undergone scattering inside the sample 12. The power of the ballistic excitation in a scattering medium can be quite high near the medium surface, but decays exponentially as it progresses toward the beam focus 22. The power density of the ballistic excitation can therefore be locally peaked at both the sample surface and at the beam focus 22.

Defining $F_S$ to be the TPEF signal 20 generated by the ballistic excitation beam near its focus, $F_B$ to be the superficial background TPEF generated by the ballistic excitation far from focus (such as near the medium surface), and $F_{NF}$ to be the near-focus background TPEF generated by scattered excitation, which, for weakly scattering media, is largely confined to a blurred area around the beam focus 22, total TPEF in a sample can be expressed by the following equation 1.

$$F_0 = F_S + F_B + F_{NF} \quad \text{(Eq. 1)}$$

As previously mentioned, when extraneous aberrations are introduced into the excitation beam path, these preferentially quench the signal TPEF ($F_S$) while leaving the background TPEF ($F_B + F_{NF}$) relatively unaffected. That is, the total TPEF with extraneous aberrations is given by the following equation 2.

$$F_\Phi \approx F_B + F_{NF} \quad \text{(Eq. 2)}$$

Subtracting equation 1 from equation 2 recovers the signal fluorescence, as illustrated by the following equation 3.

$$\Delta F = F_0 - F_\Phi \approx F_S \quad \text{(Eq. 3)}$$

The computer 54 of FIG. 2, performing functions in accordance with software stored therein, is capable of controlling types of aberrations introduced by the deformable mirror 66. Specifically, the computer 54 is capable of controlling voltage levels applied to the deformable mirror 66, thereby resulting in different types of aberrations, such as, but not limited to, quadrant and spiral phase aberrations. In addition, the computer 54 is capable of controlling timing of aberration introduction by the deformable mirror 66. Specifically, the computer 54 is capable of controlling when voltages are applied to the deformable mirror 66, thereby controlling when the deformable mirror 66 is activated.

Figure 3:
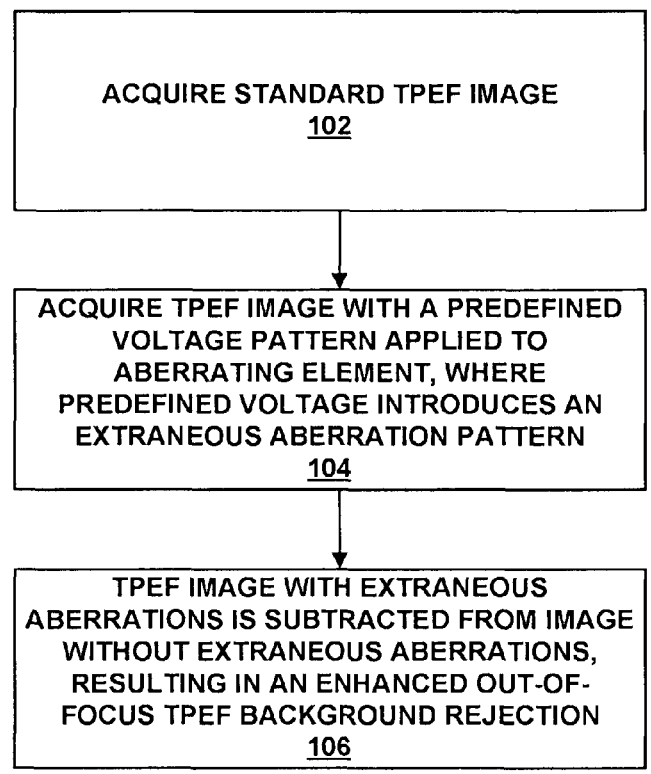
FIG. 3 is a flow chart illustrating a method of providing enhanced background rejection in thick tissue, in accordance with a first exemplary embodiment of the invention.

FIG. 3 is a flow chart 100 illustrating a method of providing enhanced background rejection in thick tissue, in accordance with a first exemplary embodiment of the invention. It should be noted that any process descriptions or blocks in flow charts should be understood as representing modules, segments, portions of code, or steps that include one or more instructions for implementing specific logical functions in the process, and alternative implementations are included within the scope of the present invention in which functions may be executed out of order from that shown or discussed, including substantially concurrently or in reverse order, depending on the functionality involved, as would be understood by those reasonably skilled in the art of the present invention.

As shown by block 102, to perform DA-TPEF a standard TPEF image is acquired by the microscope 60, without the application of deformable-mirror-induced aberrations. Specifically, a TPEF image is acquired with all deformable mirror actuator voltages set to zero volts (or to whatever voltages are required to produce a flat deformable mirror state). The flatness of the deformable mirror 66 may be verified in one or more ways. As an example, flatness of the deformable mirror 66 may be verified by characterizing the microscope resolution by acquiring images of sub-resolution sized fluorescent beads. In addition flatness of the deformable mirror 66 may be verified by measuring excitation beam phase profile at the objective back-aperture plane with a Shack-Hartmann wavefront sensor, thereby allowing for deriving of a corresponding theoretical microscope point-spread-function (PSF).

As shown by block 104, the next step in performing DA-TPEF imaging is to acquire a background image is then acquired. Specifically, a TPEF image is acquired with a pre-defined voltage pattern applied to the deformable mirror 66, where the predefined voltage pattern introduces an extraneous aberration pattern in the illumination pupil function. The resulting background image is essentially devoid of in-focus TPEF signal 20, while the background TPEF remains relatively unaffected. Stated another way, the introduction of extraneous aberrations in an illumination pupil, or objective 14, leads to a spreading of the ballistic excitation profile that is relatively more pronounced near the beam focus 22 than away from the beam focus 22, thereby preferentially quenching the in-focus TPEF signal 20, while leaving the out-of-focus TPEF background relatively unaffected.

For the background TPEF to remain relatively unaffected the same amount of total excitation power, or close to the same amount, is delivered into the sample 12 with and without DM-induced aberrations. Beam divergence imparted by the extraneous aberrations provided by the deformable mirror 66 preferably is not so large as to provoke vignetting by the illumination aperture.

In accordance with the first exemplary embodiment of the invention, there are few constraints on allowed deformable mirror induced aberration patterns, the main constraints being that the aberration patterns should provoke neither beam defocus nor tilt. For exemplary purposes, the following considers two types of aberration patterns, although it should be noted that other aberration patterns may be considered. The first aberration pattern considered is a quadrant-phase pattern where the excitation beam wavefront at the objective back aperture is divided into four quadrants, two of which are phase-shifted by $\Pi$. A second type of aberration pattern is a spiral-phase pattern, where the phase-shift imparted on the beam varies angularly from 0 to $2m\Pi$, wherein m is a small integer. Both types of aberration patterns exhibit advantages and disadvantages. The advantage of the quadrant-phase pattern is mostly technical in that it readily allows for fast DA-TPEF imaging, as explained hereinafter. Alternatively, the advantage of the spiral-phase pattern is more fundamental in that it affects out-of-focus background less than the quadrant phase pattern.

FIG. 4, comprising FIG. 4A-FIG. 4D, illustrates deformable mirror induced aberration profiles in the pupil plane (left side) and corresponding TPEF intensity distributions in the focal plane (right side), as provided by the present system and method. Referring to FIG. 4, profiles of the ballistic-excitation TPEF at the focal plane for different DM-induced aberration patterns are illustrated.

Figure 4A:
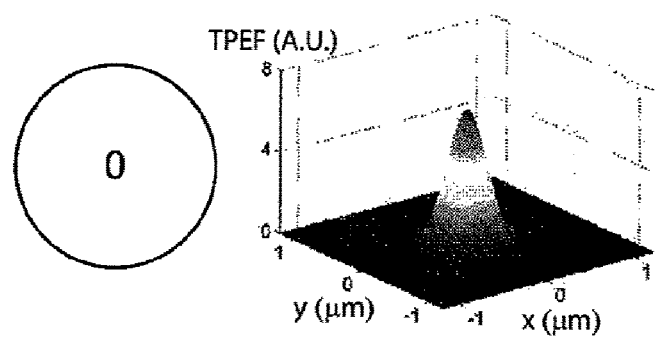
FIGS. 4A-4D illustrates deformable mirror induced aberration profiles in the pupil plane and corresponding TPEF intensity distributions in the focal plane, as provided by the system of FIG. 2.
Figure 4B:
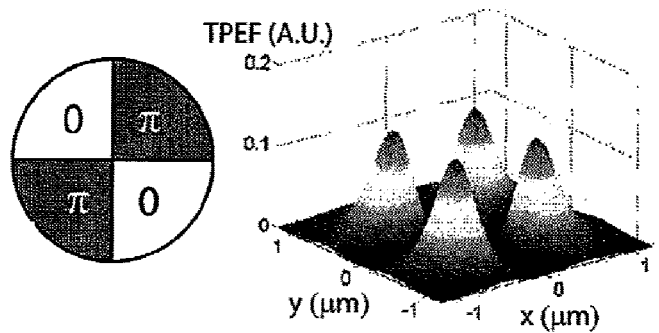
Figure 4C:
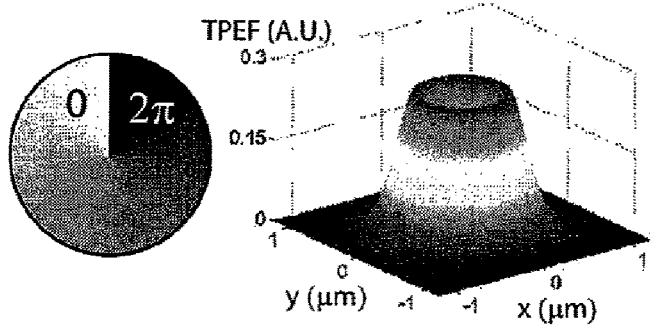
Figure 4D:
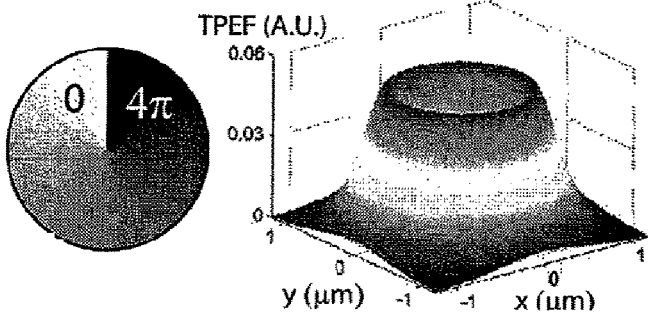

FIG. 4A provides the case where no deformable mirror induced aberrations are introduced in the illumination aperture. FIG. 4B provides the case where quadrant-phase aberrations of stroke Π are introduced in the illumination aperture by the deformable mirror. In addition, FIG. 4C provides the case where spiral-phase aberrations of pitch 2Π are introduced in the illumination aperture by the deformable mirror. Further, FIG. 4D provides the case where spiral-phase aberrations of pitch 4Π are introduced to the illumination pupil by the deformable mirror 66. The quadrant-phase pattern splits the unaberrated (i.e. diffraction-limited) TPEF peak into four sub-peaks, while the spiral-phase pattern spreads the TPEF into a ring pattern whose width spreads and whose height decreases with increasing m. Each of the patterns of aberrations leads to a TPEF null at the focal center.

Figure 5A:
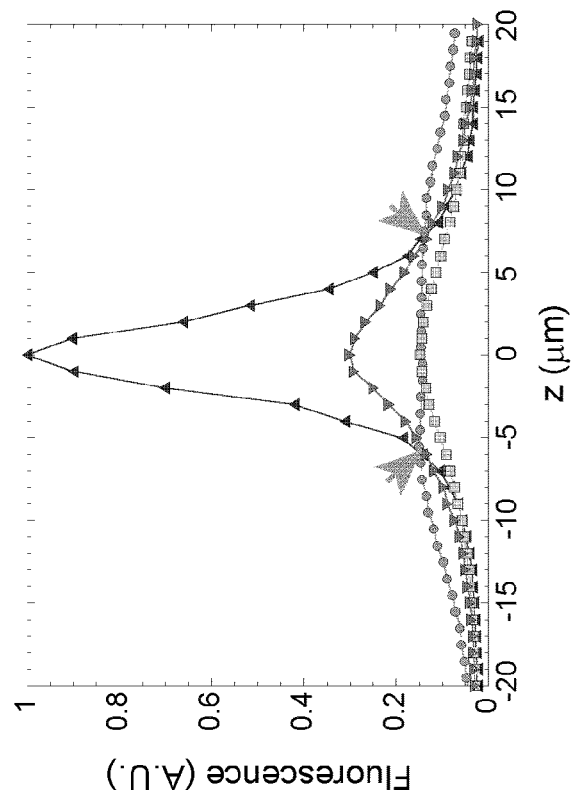
FIG. 5A and FIG. 5B illustrate the quenching of the total TPEF power generated at the focal plane is illustrated by FIG. 5A and FIG. 5B.
Figure 5B:
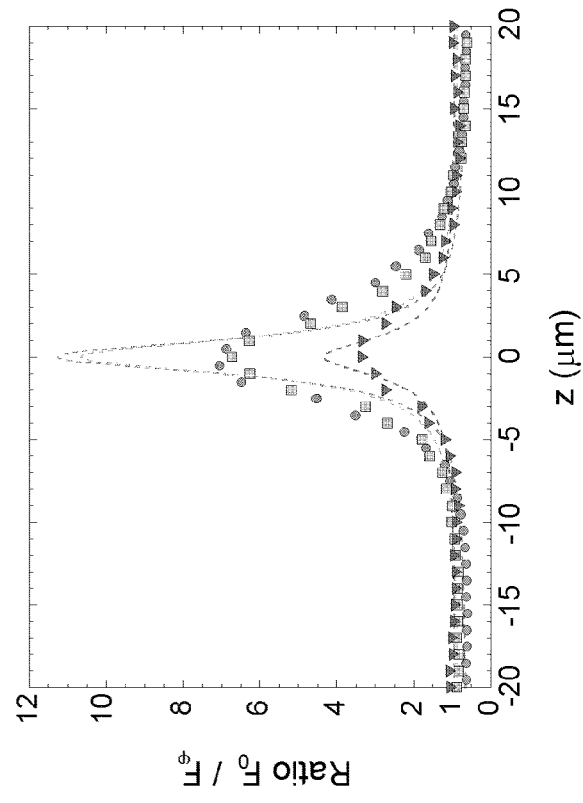

While the deformable-mirror 66 provided aberrations provoke a spread in the lateral areas of the TPEF profiles, the aberrations also provoke a significant quenching of the total TPEF power generated at the focal plane. The quenching of the total TPEF power generated at the focal plane is illustrated by FIG. 5A and FIG. 5B, which illustrate total (integrated) TPEF power generated by a thin uniform fluorescent slab as a function of slab defocus (i.e. displacement of the slab from the focal plane). In the absence of DM-induced aberrations, as shown by FIG. 5A, the TPEF power is peaked when the slab is in focus and decays as the slab is displaced from focus. When extraneous deformable mirror aberrations are introduced, the in-focus TPEF peak is severely quenched, as shown by FIG. 5B.

In FIGS. 5A and 5B the TPEF profile in the absence of deformable-mirror-induced aberrations is depicted by upward triangles, the TPEF profile having quadrant-phase pattern deformable mirror aberrations is depicted as circles, the TPEF profile having spiral-phase pattern deformable mirror aberrations with a phase shift varying angularly from 0 to 2Π is depicted as upside-down triangles, and the TPEF profile having spiral-phase pattern deformable mirror aberrations with a phase shift varying angularly from 0 to 4Π is depicted as squares. It is noted that the 2Π spiral phase aberration rejects TPEF closer to the beam focus 22 than does the 4Π spiral phase aberration, showing that the 2Π spiral phase aberration provides tighter background rejection. In practice, the choice of which spiral pitch is the most effective for DA-TPEF imaging largely depends on the sample of interest.

Returning to FIG. 3, as shown by block 106, the TPEF image with extraneous aberrations is subtracted from the image without extraneous aberrations, resulting in an enhanced out-of-focus TPEF background rejection. Subtraction of the TPEF image with extraneous aberrations from the image without extraneous aberrations is performed by the computer 54. It should be noted that one having ordinary skill in the art would know how to subtract images. As an example, basic pixel by pixel subtraction may be performed to subtract the images, or other processes may be used to perform this functionality. Since one having ordinary skill in the art would know how to subtract images, a detailed description of image subtraction is not provided herein.

It should be noted that the DA-TPEF microscope of the present invention provides images that are fundamentally different than those obtainable by simple image processing of standard TPEF microscope images. As an example, high-pass filtering of a standard TPEF microscope image would erase any low-frequency components in the image, whereas the DA-TPEF microscope of the present invention does not. Referring to FIG. 5, even though the sample is laterally homogeneous in this case, meaning that its lateral spatial frequency is equal to zero, the DA-TPEF microscope continues to reveal strong signal when the sample is in focus.

A drawback of DA-TPEF as described thus far is that two images, an unaberrated and an aberrated image, are required to obtain a final DA-TPEF image. As such, the overall image acquisition rate of a DA-TPEF microscope may be twice as slow as that of a standard TPEF microscope. Such a reduction in image acquisition rate may not be suitable when imaging fluorescence dynamics. It would be beneficial for DA-TPEF to provide the same image acquisition rate as a standard TPEF microscope. As a result, in accordance with an alternative embodiment of the invention, the present system and method introduces a strategy for fast DA-TPEF microscopy based on line-by-line DA subtraction, rather than standard frame-by-frame DA subtraction.

To mitigate the disadvantage of slower acquisition rate, the DA-TPEF microscope may be modified to benefit from dead time occasioned with standard TPEF microscope imaging. Specifically, in standard TPEF microscopes based on laser raster scans, the acquisition of data is usually one-sided, meaning that fluorescence signal is usually recorded as the laser scans along one direction, and is discarded (or the laser beam is blanked) during scan flybacks. The present system and method benefits from the flyback time, which is normally dead time, by introducing DM aberrations and acquiring the (inverted) background image during scan flybacks, thereby performing DA-TPEF line-by-line rather than frame-by-frame.

To provide the abovementioned line-by-line DA-TPEF the switching time between non-aberrated and aberrated pupil profiles as controlled by the computer 54, is made much shorter than the line-scan duration, as performed by the scanner 68. For exemplary purposes, the line-scan duration for standard galvanometric scanning is typically about 1 ms (meaning that the switching rates must be much faster than 1 kHz). Therefore, using the deformable mirror to produce pupil aberrations has a large advantage, since deformable mirrors can readily attain such switching rates. Such switching rates may be provided for by software or hardware.

While DA-TPEF can reject background, it does not increase signal. As a result, if the signal is too weak, another strategy is used to complement DA-TPEF and facilitate the extraction of signal from background. In accordance with an alternative embodiment of the invention, one such strategy, for example, involves counteracting the loss of ballistic excitation to scattering by introducing adaptive wavefront correction. Such wavefront correction has the dual benefit of both increasing signal and suppressing background, as opposed to simply rejecting background. DA-TPEF is entirely compatible with adaptive wavefront correction in that the same DM used to introduce extraneous aberrations, in accordance with the present invention, can also be used to correct the illumination wavefront.

It should be noted that, in accordance with the present invention, DA-TPEF can be operated in a simple open-loop configuration, requiring no feedback whatsoever, and no special care concerning the accuracy of the extraneous aberrations patterns.

While the abovementioned system and method focuses on the application of differential-aberration contrast to two-photon excited fluorescence microscopy, it should be noted that differential aberration contrast is not limited to this application only, and can be applied to other laser scanning nonlinear microscopy techniques, such as, but not limited to, threephoton excited fluorescence microscopy, second harmonic generation (SHG) microscopy, third harmonic generation (THG) microscopy, and even coherent anti-Stokes Raman scattering (CARS) microscopy.

The application of differential aberration contrast to coherent nonlinear microscopes (SHG, THG, CARS, etc.), is particularly interesting because of sensitivity of these microscopes to illumination phase. Since the idea of differential aberration is to impart differential extraneous phase shifts on the illumination beam, these phase shifts lead to even more dramatic changes in coherent signals (SHG, THG CARS, etc.) than in incoherent signals (fluorescence, etc.). For example, an application of differential aberration contrast to SHG microscopy is useful in differentially modulating not only SHG power but also SHG radiation patterns, which can provide valuable information on endogenous structures in tissue. In particular, the application of differential aberration can provoke modulations in the ratio of forward to backward generated SHG, providing information on density, fibril thickness, mesoscopic structure, and other information, of endogenous proteins such as, but not limited to, collagen, acto-myosin, etc. in tissue. Such an application of differential aberration contrast can be used to non-invasively assess tissue health or perform tissue diagnosis, even in thick tissue. Whether detecting in the forward and/or backward direction, the modulation of radiation patterns by differential aberration contrast can be monitored by a single detector, or more accurately by two or more detectors, or even a CCD camera.

It should be noted that the DA-TPEF of the present invention are appealing due to their simplicity and robustness. DA-TPEF can be combined with any TPEF microscope by insertion of a controllable and switchable aberrating element into the illumination beam path, provided this element is imaged onto the illumination pupil. Moreover, DA-TPEF can be operated in a simple open-loop configuration, requiring no feedback whatsoever, and no special care concerning the accuracy of the extraneous aberrations patterns.

It should be emphasized that the above-described embodiments of the present invention are merely possible examples of implementations, merely set forth for a clear understanding of the principles of the invention. Many variations and modifications may be made to the above-described embodiments of the invention without departing substantially from the spirit and principles of the invention. All such modifications and variations are intended to be included herein within the scope of this disclosure and the present invention and protected by the following claims.

What is claimed is:

1. An apparatus for providing enhanced background rejection in thick tissue, comprising:
    an aberrating element located in an excitation beam path of the apparatus, wherein the aberrating element is capable of introducing controllable extraneous spatial aberrations in the excitation beam path of the apparatus;
    at least one mirror capable of directing received laser pulses to the aberrating element;
    an objective;
    a beam scanner imaged onto a back aperture of the objective so that the beam scanner steers beam focus within the thick tissue; and
    a detector for recording signals produced by the tissue,
    wherein there is no communication between the deformable mirror aberrating element and the detector, and as a result, patterns are applied to the aberrating element that are independent of what is received by the detector, and
    wherein the patterns are predefined and independent of any a priori information regarding the sample and the system settings.

2. The apparatus of claim 1, wherein the aberrating element is a deformable mirror.

3. The apparatus of claim 1, further comprising a dichroic mirror capable of separating laser illumination from a signal produced from the tissue.

4. The apparatus of claim 1, wherein the detector is a photomultiplier tube.

5. The apparatus of claim 1, wherein the aberrating element is located in a conjugate plane of the objective back aperture.

6. The apparatus of claim 1, further comprising a laser source.

7. The apparatus of claim 6, wherein the laser source is a pulse laser source.

8. The apparatus of claim 1, further comprising a computer capable of controlling the aberrating element so as to control timing of aberration introduced by the aberrating element.

9. The apparatus of claim 1, further comprising a computer capable of controlling a type of aberration provided by the aberrating element.

10. A method of providing enhanced thick tissue background rejection in microscopy, comprising the steps of:
    acquiring a standard two-photon excited fluorescence of the thick tissue without introducing extraneous aberrations;
    introducing an extraneous aberration pattern in an excitation beam path, wherein the extraneous aberration pattern is provided by an aberrating element;
    acquiring two-photon excited fluorescence of the thick tissue having the introduced extraneous aberration pattern, providing a two-photon excited fluorescence with extraneous aberrations; and
    subtracting the two-photon excited fluorescence with extraneous aberrations from the acquired standard two-photon excited fluorescence of the thick tissue without extraneous aberrations resulting in an enhanced out-of-focus two-photon excited fluorescence background rejection,
    wherein acquiring of the standard two-photon excited fluorescence of the thick tissue without introducing extraneous aberrations and acquiring the two-photon excited fluorescence of the thick tissue having the introduced extraneous aberration pattern are performed by use of a detector, and
    wherein there is no communication between the aberrating element and the detector, and as a result, patterns are applied to the aberrating element that are independent of what is received by the detector, and
    wherein the patterns are predefined and independent of any a priori information regarding the sample and the system settings.

11. The method of claim 10, wherein the aberrating element is a deformable mirror.

12. The method of claim 11, wherein flatness of the deformable mirror when no aberrations are introduced is verified by measuring excitation beam phase profile at an objective back-aperture plane with a wavefront sensor.

13. The method of claim 10, wherein close to the same amount of total excitation power is delivered into the thick tissue with and without extraneous aberrations.

14. The method of claim 10, wherein the extraneous aberration pattern is selected from the group consisting of a quadrant-phase pattern and a spiral-phase pattern.

15. The method of claim 10, wherein the step of subtracting is performed by using pixel by pixel subtraction.

16. The method of claim 10, wherein the step of subtraction is further defined as using line-by-line differential aberration subtraction.

* * * * *